United States Patent [19]

Nadelson

[11] 4,054,653

[45] Oct. 18, 1977

[54] SUBSTITUTED PYRIDO[3,4-E]OXAZINE DIONES AND THEIR THERAPEUTIC USE

[75] Inventor: Jeffrey Nadelson, Lake Parsippany, N.J.

[73] Assignee: Sandoz, Inc., E. Hanover, N.J.

[21] Appl. No.: 691,529

[22] Filed: June 1, 1976

[51] Int. Cl.$^2$ .................. A01N 9/00; A01N 9/22; C07D 265/00; C07D 273/00
[52] U.S. Cl. .................. 424/248.57; 544/91
[58] Field of Search .................. 260/244; 424/248.4, 424/248.51, 248.56, 248.57

[56] References Cited

U.S. PATENT DOCUMENTS

| | | | |
|---|---|---|---|
| 3,122,538 | 2/1964 | Clauson-Kaas et al. | 260/244 |
| 3,905,956 | 9/1975 | Derieg et al. | 260/239.3 T |

*Primary Examiner*—Albert T. Meyers
*Assistant Examiner*—D. W. Robinson
*Attorney, Agent, or Firm*—Gerald D. Sharkin; Robert S. Honor; Timothy G. Rothwell

[57] ABSTRACT

Substituted pyrido[3,4-e]oxazine diones, e.g., 6-methyl-4,7-diphenyl-2H-pyrido[3,4-e]-1,3-oxazine-2,5-dione are useful as minor tranquilizers, sleep inducers and muscle relaxants.

10 Claims, No Drawings

SUBSTITUTED PYRIDO[3,4-E]OXAZINE DIONES AND THEIR THERAPEUTIC USE

This invention relates to substituted pyrido[3,4-e] oxazine diones which exhibit minor tranquilizer, sleep inducer and muscle relaxant activity. In particular, it relates to pyrido[3,4-e]-1,3-oxazine-2,5-diones, and to the processes for their preparation.

The compounds of this invention may be represented by the following structural formula:

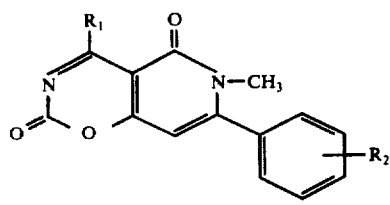

(I)

wherein $R_1$ represents straight chain lower alkyl, i.e. alkyl having 1 to 4 carbon atoms, e.g., methyl, ethyl, propyl and the like, or

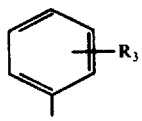

where $R_3$ represents hydrogen, or halo having an atomic weight of about 19 to 36, and $R_2$ is hydrogen, or halo having an atomic weight of about 19 to 36.

The compounds of formula (I) are prepared according to the following reaction scheme:

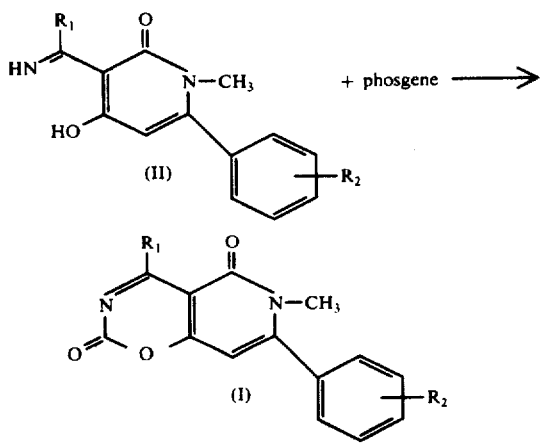

where $R_1$ and $R_2$ are as defined above.

The compounds of formula (I) are prepared by reacting a compound of the formula (II) with phosgene in the presence of an acid binding agent such as pyridine, diisopropyl ethyl amine or triethylamine, preferably triethylamine, in the presence of an inert anhydrous organic solvent. Although the particular anhydrous solvent used is not critical, the preferred solvents include the halogenated hydrocarbons such as methylene chloride carbon tetrachloride, chloroform and the like, or the aromatic hydrocarbons such as benzene, toluene and the like, preferably toluene. The temperature of the reaction is not critical, but it is preferred that the reaction be run from about 20° to 80° C., preferably from about 25° to 40° C. The reaction is run from about 10 to 36 hours, preferably from about 16 to 24 hours. The product is recovered using conventional techniques, e.g., recrystallization.

The compounds of formula (II) are prepared according to the following reaction scheme:

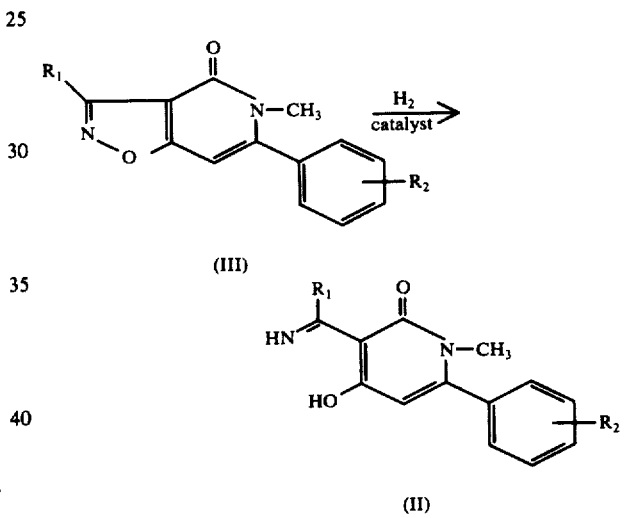

where $R_1$ and $R_2$ are as defined above.

The compounds of formula (II) are prepared by reducing a compound of the formula (III) under hydrogen gas in the presence of a catalyst and an inert organic solvent. Although the particular hydrogenation catalyst employed is not critical, the preferred catalysts include palladium on carbon, platinum oxide, Raney nickel, and the like, preferably palladium on carbon. The particular solvent used is not critical, but it is preferred that the reaction be run in the presence of the lower alkanols, e.g., methanol, ethanol, and the like, preferably ethanol. The temperature of the reaction is not critical, but it is preferred that the reaction be run from about 10° to 50° C., preferably from about 20° to 30° C. The reaction is run from about 1 to 10 hours, preferably from about 2 to 3 hours. The product is recovered using conventional techniques, e.g., filtration.

The compounds of formula (III) are prepared according to the following reaction scheme:

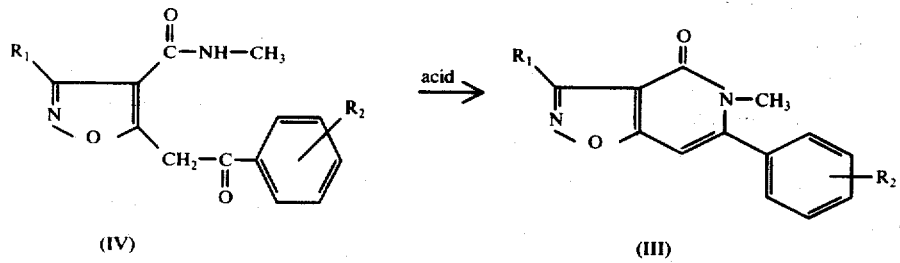

where $R_1$ and $R_2$ are as defined above.

The compounds of formula (III) are prepared by treating a compound of the formula (IV) with an acid, such as hydrochloric acid, p-toluenesulfonic acid, polyphosphoric acid or sulfuric acid, the latter being especially preferred, in the presence of an inert solvent. Although the particular solvent employed is not critical, the preferred solvents include the aromatic hydrocarbons, such as benzene, toluene and the like, or an excess of the acid utilized above, the latter being espeployed is critical, and water is the only solvent contemplated in this reaction. The temperature of the reaction is not critical, but it is preferred that the reaction be run from about 10° to 50° C., preferably from about 20° to 30° C. The reaction is run from about 1 to 5 hours, preferably from about 1.5 to 2.5 hours. The product is recovered using conventional techniques, e.g., trituration followed by filtration.

The compounds of formula (V) are prepared according to the following reaction scheme:

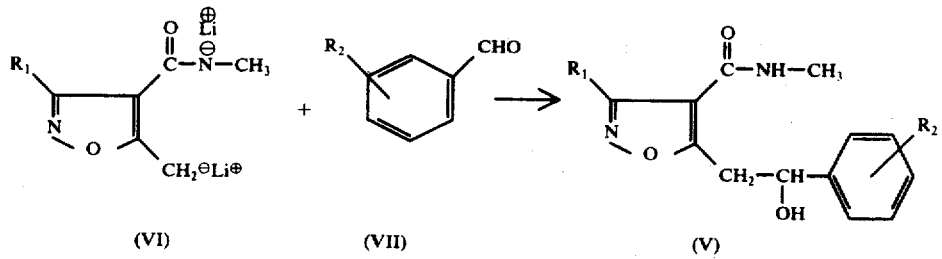

cially preferred. The temperature of the reaction is not critical, but it is preferred that the reaction be run from about 80° to 150° C., preferably the reflux temperature of the solvent. The reaction is run from about 12 to 36 hours, preferably from about 20 to 36 hours. The product is recovered using conventional techniques, e.g., trituration followed by recrystallization.

The compounds of formula (IV) are prepared in accordance with the following reaction scheme:

where $R_1$ and $R_2$ are as defined above.

The compounds of formula (V) are prepared by treating a compound of the formula (VI) with a compound of the formula (VII) in the presence of an inert organic solvent. Although the particular solvent employed is not critical, the preferred solvents include an ether such as diethylether or tetrahydrofuran or an aliphatic hydrocarbon such as pentene, hexane, heptane and the like, preferably tetrahydrofuran. The temperature of

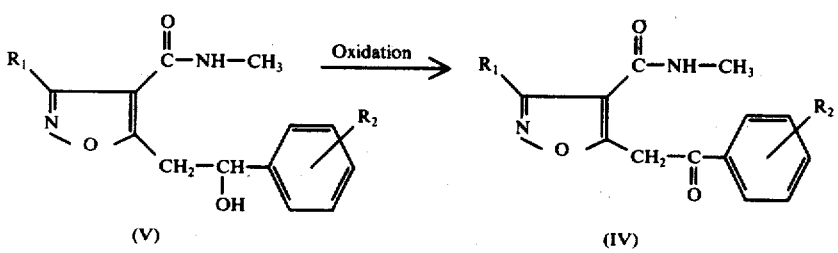

where $R_1$ and $R_2$ are as defined above.

The compounds of formula (IV) are prepared by treating a compound of the formula (V) with an oxidizing agent such as chromium trioxide, potassium permanganate, and the like, preferably chromium trioxide, under acidic conditions in the presence of water. Although the particular acid employed is not critical, the preferred acids include the mineral acids such as sulfuric acid, hydrochloric acid or acetic acid, the latter being especially preferred. The particular solvent emthe reaction is not critical, but it is preferred that the reaction be run at a temperature of from about −75° to −55° C., preferably from about −65° to −60° C. The reaction is run from about 1 to 5 hours, preferably from about 2.5 to 3.5 hours. The product is recovered using conventional techniques, e.g., trituration followed by filtration.

The compounds of formula (VI) are prepared according to the following reaction scheme:

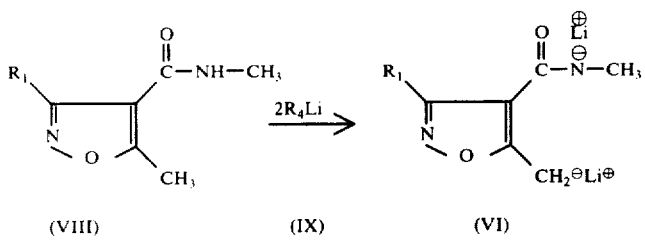

(VIII)    (IX)    (VI)

where
R$_4$ is lower alkyl having 1 to 4 carbon atoms, and
R$_1$ is as defined above.

The compounds of formula (VI) are prepared by treating a compound of the formula (VIII) with a compound of the formula (IX) in the presence of an inert organic solvent. Although the particlar solvent employed is not critical, the preferred solvents include an ether such as diethylether or tetrahydrofuran as an aliphatic hydrocarbon such as pentane, hexane, heptane and the like, preferably hexane. The temperature of the reaction is not critical, but it is preferred that the reaction be run at a temperature of from about −75° to −55° C., preferably from about −65° to −60° C. The reaction is run from about 1 to 5 hours, preferably from about 2.5 to 3.5 hours. The product of the compound of formula (VIII) is not isolated but employed in situ as a starting material in the preparation of the compounds of formula (V).

Many of the compounds of formulae (VII), (VIII), and (IX) are known and may be prepared by methods described in the literature. The compounds of formulae (VII), (VIII), and (IX) not specifically described may be prepared by analogous methods from known starting materials.

The compounds of formula (I) are useful because they possess pharmacological activity in animals as sleep inducers, minor tranquilizers and muscle relaxants as indicated (1) by the hexobarbital reinduction method of Winter, J. Pharmacol. and Exp. Therap., 94, 7–11, 1948, in which the reinduction of anethesia is used to determine sedativehypnotic activity in mice given 70 mg/kg of animal body weight i.p. of hexobarbital followed immediately after the mice regain their righting reflexes by 10.4 to 200 mg/kg of animal body weight i.p. of the test compound; (2) by their ability to produce docility in behavior tests in mice given 20 to 200 mg/kg of animal body weight, i.p. of the test compound according to the 30-word adjective check sheet system basically as described by Irwin S. (gordon Research Conference, Medicinal Chemistry, 1959) and Chen (Symposium on Sedative and Hypnotic Drugs, Williams and Wilkins, 1954); (3) by their ability to antagonize chlonic convulsions and death in mice given about 13.3 to 250 mg/kg of the test compound followed immediately by 50 mg/kg i.p. of N-sulfamoylazepine; (4) by scoring for loss of righting reflex according to the method of Reed-Muench (American Journal of Hygiene, 27: 493–497, 1938), in which mice are administered 12.5 mg/kg i.p. Thioridazine, immediately after which the test compound is administered at dosages of 16.5 to 100 mg/kg in a volume of 0.1 ml/10 g. body weight. Sixty minutes after dosing, the mice are scored for loss of righting reflex; and (5) by the rotarod test as described by Dunham and Miya (J. Am. Pharm.. Assoc., 45: 208, 1957).

The sleep inducing effective dosage of the compounds of formula (I) will vary depending on the particular compound employed. However, in general, satisfactory results are obtained when the compounds are administered orally at a daily dosage of from about 1.0 milligram to about 100 milligrams per kilogram of animal body weight, typically given in a single dose at bedtime. For most large mammals, the total daily dosage is from about 10 to about 500 milligrams, preferably at bedtime and dosage forms suitable for internal administration comprise from about 2.5 to about 250 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

For minor tranquilizer use in the treatment of anxiety and tension, the effective dosage will vary depending on the particular compound employed. However, in general, satisfactory results are obtained when the compounds are administered orally at a daily dosage of from about 1.0 milligram to about 200 milligrams per kilogram of animal body weight, typically given in divided doses two to four times per day. For most large mammals, the total daily dosage is from about 10 to about 500 milligrams, and dosage forms suitable for internal administration comprise from about 2.5 to about 250 milligrams of the compound in admixture with a solid or liquid pharmaceutical carrier or diluent.

For muscle relaxant use in the treatment of muscle spasms, the effective dosage will vary depending on the particular compound employed. However, in general, satisfactory results are obtained when the compounds are administered orally at a daily dosage of from about 1.0 milligram to about 200 milligrams per kilogram of animal body weight, typically given in divided doses two to four times per day. For most large mammals, the total daily dosage is from about 10 to about 1000 milligrams and dosage forms suitable for internal administration comprise from about 2.5 to about 500 milligrams of the compound in admixture with a solid or liquid pharmaceutical carrier or diluent.

Tablets and capsules containing the ingredients indicated below may be prepared by conventional techniques and are useful as sleep inducers at a dose of one or two tablets just before bedtime. Tablets and capsules containing the ingredients indicated below may also be useful as minor tranquilizers and muscle relaxants in divided doses two to four times per day.

| Ingredients | Weight (mg.) tablet | capsule |
|---|---|---|
| 6-methyl-4,7-diphenyl-2H-pyrido[3,4-e]-1,3-oxazine-2,5-dione | 200 | 200 |
| tragacanth | 10 | — |
| lactose | 247.5 | 300 |
| corn starch | 25 | — |
| talcum | 15 | — |
| magnesium stearate | 2.5 | — |
| TOTAL | 500 mg. | 500 mg. |

EXAMPLE 1.

3-Phenyl-5-(β-hydroxyphenethyl)-N-methyl-isoxazole-4-carboxamide.

A suspension of 75 g. (0.348 mole) of 3-phenyl-5-N-dimethyl-isoxazole-4-carboxamide and 1 liter of tetrahydrofuran is cooled to −65° C. and 478 ml. of 1.6M n-butyllithium in hexane (0.765 mole) is added dropwise maintaining the temperature between −60° and −70° C. After the addition is complete, the orange suspension is stirred for 1½ hours at −60° to −70° C., and then 37.2 g. (0.350 mole) of benzaldehyde in 375 ml. tetrahydrofuran is added dropwise maintaining the temperature between −60° and −70° C. After addition is complete, the mixture is stirred 1½ hours at −60° to −70° C. and then warmed to −30° C. and quenched by the addition of saturated ammonium chloride solution. The mixture is further diluted with tetrahydrofuran and the layers are separated. The tetrahydrofuran layer is washed twice with 50% brine, and once with brine, dried over anhydrous magnesium sulfate, filtered and evaporated in vacuo. The solid residue is triturated with a 50:50 mixture of ether:petroleum ether, filtered and washed with cold ether to give 3-phenyl-5-(β-hydroxyphenethyl)-N-methyl-isoxazole-4-carboxamide, m.p. 183°–184° C.

Following the above procedure and using in place of 3-phenyl-5,N-dimethyl-isoxazole-4-carboxamide, an equivalent amount of a. 3-(p-chlorophenyl)-5,N-dimethyl-isoxazole-4-carboxamide,
    b. 3-(p-fluorophenyl)-5,N-dimethyl-isoxazole-4-carboxamide, or
    c. 3-ethyl-5,N-dimethyl-isoxazole-4-carboxamide there is obtained a. 3-(p-chlorophenyl)-5-(β-hydroxyphenethyl)-N-methyl-isoxazole-4-carboxamide,
    b. 3-(p-fluorophenyl)-5-(β-hydroxyphenethyl)-N-methyl-isoxazole-4-carboxamide, or
    c. 3-ethyl-5-(β-hydroxyphenethyl)-N-methyl-isoxazole-4-carboxamide, respectively.

Again following the same procedure and using in place of benzaldehyde an equivalent amount of d. p-chlorobenzaldehyde,
    e. p-fluorobenzaldehyde,
    f. m-fluorobenzaldehyde, or
    g. o-fluorobenzaldehyde there is obtained d. 3-phenyl-5-(4-chloro-β-hydroxyphenethyl)-N-methyl-isoxazole-4-carboxamide,
    e. 3-phenyl-5-(4-fluoro-β-hydroxyphenethyl)-N-methyl-isoxazole-4-carboxamide,
    f. 3-phenyl-5-(3-fluoro-β-hydroxyphenethyl)-N-methyl-isoxazole-4-carboxamide, or
    g. 3-phenyl-5-(2-fluoro-β-hydroxyphenethyl)-N-methyl-isoxazole-4-carboxamide, respectively.

Furthermore, following the same procedure as outlined above and using in place of 3-phenyl-5,N-dimethyl-isoxazole-4-carboxamide an equivalent amount of 3-ethyl-5,N-dimethylisoxazole-4-carboxamide, and in place of benzaldehyde an equivalent amount of d. p-chlorobenzaldehyde,
    e. p-fluorobenzaldehyde,
    f. m-fluorobenzaldehyde, or
    g. o-fluorobenzaldehyde there is obtained h. 3-ethyl-5-(4-chloro-β-hydroxyphenethyl)-N-isoxazle-4-carboxamide,
    i. 3-ethyl-5-(4-fluoro-β-hydroxyphenethyl)-N-methyl-isoxazole-4-carboxamide,
    j. 3-ethyl-5-(3-fluoro-β-hydroxyphenethyl)-N-methyl-isoxazole-4-carboxamide, or
    k. 3-ethyl-5-(2-fluoro-β-hydroxyphenethyl)-N-methyl-isoxazole-4-carboxamide, respectively.

Also following the above procedure and using in place of 3-phenyl-5,N-dimethyl-isoxazole-4-carboxamide, an equivalent amount of 3-(p-fluorophenyl)-5,N-dimethyl-isoxazole-4-carboxamide, and in place of benzaldehyde an equivalent amount of p-fluorobenzaldehyde, there is obtained l. 3-(p-fluorophenyl)-5-(4-fluoro-β-hydroxyphenethyl)-N-methyl-isoxazole-4-carboxamide.

EXAMPLE 2.

N-methyl-5-phenacyl-3-phenyl-4-isoxazole carboxamide.

A suspension of 50 g. (0.155 mole) of 3-phenyl-5-(β-hydroxyphenethyl)-N-methyl-isoxazole-4-carboxamide and 800 ml. acetic acid at room temperature is treated dropwise rapidly with 18.4 g. (0.185 mole) of chromium trioxide in 185 ml. water. The resulting solution is stirred for 2 hours at room temperature and a portion of the acetic acid is removed in vacuo. The remainder is poured onto ice water and extracted with methylene chloride. The methylene chloride layer is washed with 2N sodium hydroxide, dried over anhydrous magnesium sulfate, filtered and evaporated in vacuo. The solid residue is triturated with hot ether, cooled to 0° C. and filtered to give N-methyl-5-phenacyl-3-phenyl-4isoxazole carboxamide, m.p. 125° to 128° C.

Following the above procedure and using in place of 3-phenyl-5-(β-hydroxyphenethyl)-N-methyl-isoxazole-4-carboxamide, an equivalent amount of a. 3-(p-chlorophenyl)-5-(β-hydroxyphenethyl)-N-methyl-isoxazole-4-carboxamide,
    b. 3-(p-fluorophenyl)-5-(β-hydroxyphenethyl)-N-methyl-isoxazole-4-carboxamide,
    c. 3-ethyl-5-(β-hydroxyphenethyl)-N-methyl-isoxazole-4-carboxamide,
    d. 3-phenyl-5-(4-chloro-β-hydroxyphenethyl)-N-methyl-isoxazole-4-carboxamide,
    e. 3-phenyl-5-(4-fluoro-β-hydroxyphenethyl)-N-methyl-isoxazole-4-carboxamide,
    f. 3-phenyl-5-(3-fluoro-β-hydroxyphenethyl)-N-methyl-isoxazole-4-carboxamide,
    g. 3-phenyl-5-(2-fluoro-β-hydroxyphenethyl)-N-methyl-isoxazole-4-carboxamide,
    h. 3-ethyl-5-(4-chloro-β-hydroxyphenethyl)-N-methyl-isoxazole-4-carboxamide,
    i. 3-ethyl-5-(4-fluoro-β-hydroxyphenethyl)-N-methyyl-isoxazole-4-carboxamide,
    j. 3-ethyl-5-(3-fluoro-β-hydroxyphenethyl)-N-methyl-isoxazole-4-carboxamide,
    k. 3-ethyl-5(2-fluoro-β-hydroxyphenethyl)-N-methyl-isoxazole-4-carboxamide, or
    l. 3-(p-fluorophenyl)-5-(4-fluoro-β-hydroxyphenethyl)-N-methyl-isoxazole-4-carboxamide, there is obtained a. N-methyl-5-phenacyl-3-(p-chlorophenyl)-4-isoxazole carboxamide,
    b. N-methyl-5-phenacyl-3-(p-fluorophenyl)-4-isoxazole carboxamide, c. 3-ethyl-N-methyl-5-phenacyl-4-isoxazole carboxamide,
d. N-methyl-5-(4-chlorophenacyl)-3-phenyl-4-isoxazole carboxamide,
e. N-methyl-5-(4-fluorophenacyl)-3-phenyl-4-isoxazole carboxamide,
f. N-methyl-5-(3-fluorophenacyl)-3-phenyl-4-isoxazole carboxamide,
g. N-methyl-5-(2-fluorophenacyl)-3-phenyl-4-isoxazole carboxamide,
h. 3-ethyl-N-methyl-5-(4-chlorophenacyl)-4-isoxazole carboxamide,
i. 3-ethyl-N-methyl-5-(4-fluorophenacyl)-4-isoxazole carboxamide,
j. 3-ethyl-N-methyl-5-(3-fluorophenacyl)-4-isoxazole carboxamide,
k. 3-ethyl-N-methyl-5-(2-fluorophenylacyl)-4-isoxazole carboxamide, or
l. N-methyl-5-(4-fluorophenacyl)-3-(p-fluorophenyl)-4-isoxazole carboxamide, respectively.

EXAMPLE 3.

5-Methyl-3,6-diphenyl-isoxazolo[4,5-c]pyridin-4(5H)-one

A mixture of 26.1 g. (0.0815 mole) of N-methyl-5-phenacyl-3-phenyl-4-isoxazole carboxamide and 261 ml. of 2M sulfuric acid is refluxed for 24 hours. The mixture is cooled and extracted with methylene chloride. The methylene chloride layer is washed with water and then brine, dried over anhydrous magnesium sulfate, filtered and evaporated in vacuo. The residue is triturated with ether and then recrystallized from ethanol to give 5-methyl-3,6-diphenyl-isoxazolo[4,5-c]pyridin-4(5H)-one, m.p. 149°–151.5° C.

Following the above procedure and using in place of N-methyl-5-phenacyl-3-phenyl-4-isoxazole carboxamide, an equivalent amount of
 a. N-methyl-5-phenacyl-3-(p-chlorophenyl)-4-isoxazole carboxamide,
 b. N-methyl-5-phenacyl-3-(p-fluorophenyl)-4-isoxazole carboxamide,
 c. 3-ethyl-N-methyl-5-phenacyl-4-isoxazole carboxamide,
 d. N-methyl-5-(4-chlorophenacyl)-3-phenyl-4-isoxazole carboxamide,
 e. N-methyl-5-(4-fluorophenacyl)-3-phenyl-4-isoxazole carboxamide,
 f. N-methyl-5-(3-fluorophenacyl)-3-phenyl-4-isoxazole carboxamide,
 g. N-methyl-5-(2-fluorophenacyl)-3phenyl-4-isoxazole carboxamide,
 h. 3-ethyl-N-methyl-5-(4-chlorophenacyl)-4-isoxazole carboxamide,
 i. 3-ethyl-N-methyl-5-(4-fluorophenacyl)-4-isoxazole carboxamide,
 j. 3-ethyl-N-methyl-5-(3-fluorophenacyl)-4-isoxazole carboxamide,
 k. 3-ethyl-N-methyl-5-(2-fluorophenacyl)-4-isoxazole carboxamide, or
 l. N-methyl-5-(4-fluorophenacyl)-3-(p-fluorophenyl)-4-isoxazole carboxamide
there is obtained
 a. 5-methyl-3-(p-chlorophenyl)-6-phenyl isoxozolo[4,5-c]pyridin-4(5H)-one,
 b. 5-methyl-3-(p-fluorophenyl)-6-phenyl-isoxozolo[4,5-c]pyridin-4(5H)-one,
 c. 3-ethyl-5-methyl-6-phenyl-isoxazolo[4,5-c]pyridin-4(5H)-one,
 d. 5-methyl-3-phenyl-6-(p-chlorophenyl)-isoxazolo[4,5-c]pyridin-4-(5H)-one,
 e. 5-methyl-3-phenyl-6-(p-fluorophenyl)-isoxazolo[4,5-c]pyridin-4(5H)-one,
 f. 5-methyl-3-phenyl-6-(m-fluorophenyl)-isoxazolo[4,5-c]pyridin-4(5H)-one,
 g. 5-methyl-3-phenyl-6-(o-fluorophenyl)-isoxazolo[4,5-c]pyridin-4(5H)-one,
 h. 3-ethyl-5-methyl-6-(p-chlorophenyl)-isoxazolo[4,5-c]pyridin-4(5H)-one,
 i. 3-ethyl-5-methyl-6-(p-fluorophenyl)-isoxazolo[4,5-c]pyridin-4(5H)-one,
 j. 3-ethyl-5-methyl-6-(m-flourophenyl)-isoxazolo[4,5-c]pyridin-4(5H)-one,
 k. 3-ethyl-5-methyl-6-(o-fluorophenyl)-isoxazolo[4,5-c]pyridin-4(5H)-one, or
 l. 5-methyl-3-(p-fluorophenyl)-6-(p-fluorophenyl)isoxazolo[4,5-c]pyridin-4(5H)-one, respectively.

EXAMPLE 4.

3-(α-iminobenzyl)-4-hydroxy-6-phenyl-1-methyl-2-(1H)-pyridone

A mixture of 16.5 g. (.0545 mole) of N-methyl-3,6-diphenyl-isoxazolo[4,5-c]pyridin-4(5H)-one, 330 ml. ethanol and 1.65 g. 10% palladium on carbon is hydrogenated at 50 psi and room temperature. The hydrogenation is ceased after 1 equivalent of hydrogen is absorbed (ca 2.5 hours). The mixture is treated with methylene chloride and the catalyst is removed by filtration. The solvents are removed in vacuo to a volume of ca. 50 ml. and then ether is added, to precipitate solids which are removed by filtration to give 3-(α-iminobenzyl)-4-hydroxy-6-phenyl-1-methyl-2(1H)-pyridone, m.p. 238°–240° C. The above compound is dissolved in methanol and treated with sodium hydroxide solution to yield after evaporation the sodium salt of 3-(α-iminobenzyl)-4-hydroxy-6-phenyl-1-methyl-2-(1H)-pyridone.

Following the above procedure and using in place of N-methyl-3,6-diphenyl-isoxazolo[4,5-c]pyridin-4(5H)-one, an equivalent amount of
 a. 5-methyl-3-(p-chlorophenyl)-6-phenyl-isoxazolo[4,5-c]pyridin-4-(5H)-one,
 b. 5-methyl-3-(p-fluorophenyl)-6-phenyl-isoxazolo[4,5-c]pyridin-4(5H)-one,
 c. 3-ethyl-5-methyl-6-phenyl-isoxazolo[4,5-c]pyridin-4(5H)-one,
 d. 5-methyl-'-phenyl-6-(p-chlorophenyl)-isoxazolo[4,5-c]pyridin-4(5H)-one,
 e. 5-methyl-3-phenyl-6-(p-fluorophenyl)-isoxazolo[4,5-c]pyridin-4(5H)-one,
 f. 5-methyl-4-phenyl-6-(m-fluorophenyl)-isoxazolo[4,5-c]pyridin-4(5H)-one,
 g. 5-methyl-3-phenyl-6-(o-fluorophenyl)-isoxazolo[4,5-c]pyridin-4(5H)-one,
 h. 3-ethyl-5-methyl-6-(p-chlorophenyl)-isoxazolo[4,5-c]pyridin-4(5H)-one,
 j. 3-ethyl-5-methyl-6-)p-fluorophenyl)-isoxazolo[4,5-c]pyridin-4(5H)-one,
 j. 3-ethyl-5-methyl-6-(m-fluorophenyl)-isoxazolo[4,5-c]pyridin-4(5H)-one,
 k. 3-ethyl-5-methyl-6-(o-fluorophenyl)-isoxazolo[4,5-c]pyridin-4(5H)-one, or
 l. 5-methyl-3-(p-fluorophenyl)-6-(p-fluorophenyl)-isoxazolo[4,5-c]pyridin-4(5H)-one there is obtained
a. 3-(α-imino-p-chlorobenzyl)-4-hydroxy-6-phenyl-1-methyl-2(1H)-pyridone,
b. 3-(α-imino-p-fluorobenzyl)-4-hydroxy-6-phenyl-1-methyl-2(1H)-pyridone,
c. 3-(1-iminopropyl)-4-hydroxy-6-phenyl-1-methyl-2(1H)-pyridone,
d. 3-(α-iminobenzyl)-4-hydroxy-6-(p-chlorophenyl)-1-methyl-2-(1H)-pyridone,
e. 3-(α-iminobenzyl)-4-hydroxy-6-(p-fluorophenyl)-1-methyl-2-(1H)-pyridone,
f. 3-(α-iminobenzyl)-4-hydroxy-6-(m-fluorophenyl)-1-methyl-2-(1H)-pyridone,
g. 3-(α-iminobenzyl)-4-hydroxy-6-(o-fluorophenyl)-1-methyl-2(1H)-pyridone,
h. 3-(1-iminopropyl)-4-hydroxy-6-(p-chlorophenyl)-1-methyl-2-(1H)-pyridone,
i. 3-(1-iminopropyl)-4-hydroxy-6-(p-fluorophenyl)-1-methyl-2-(1H)-pyridone,
j. 3-(1-iminopropyl)-4-hydroxy-6-(m-fluorophenyl)-1-methyl-2(1H)-pyridone,
k. 3-(1-iminopropyl)-4-hydroxy-6-(o-fluorophenyl)-1-methyl-2(1H)-pyridone, or
l. 3-(α-imino-p-fluorobenzyl)-4-hydroxy-6-(p-fluorophenyl)-1-methyl-2(1H)-pyridone, respectively.

EXAMPLE 5

6-Methyl-4,7-diphenyl-2H-pyrido[3,4-e]-1,3-oxazine-2,5-dione

A mixture of 10 g. (0.0348 mole) of 3-(α-iminobenzyl)-4-hydroxy-6-phenyl-1-methyl-2(1H)-pyridone and 7.3 g. (0.0724 mole) triethylamine in 200 ml. toluene is treated portionwise with 30 ml. (27.8 g., 0.0348 mole) of a 12.5% solution of phosgene in benzene. The resulting mixture becomes warm and the solids are separated out. The mixture is then stirred at room temperture for 18 hours and then poured onto water and filtered. The solids are washed with toluene. The toluene and water filtrate is separated and the toluene dried over anhydrous magnesium sulfate, filtered and evaporated in vacuo. The resulting solid is recrystallized with hot toluene to give 6-methyl-4,7-diphenyl-2H-pyrido[3,4-e]-1,3-oxazine-2,5-dione, m.p. 178°–179° C.

Following the above procedure and using in place of 3-(α-iminobenzyl)-4-hydroxy-6-phenyl-1-methyl-2(1H)-pyridone an equivalent amount of
a. 3-(α-imino-p-chlorobenzyl)-4-hydoxy-6-phenyl-1-methyl-2(1H)-pyridone,
b. 3-(α-imino-p-fluorobenzyl)-4-hydroxy-6-phenyl-1-methyl-2(1H)-pyridone,
c. 3-(1-iminopropyl)-4-hydroxy-6-phenyl-1-methyl-2(1H)-pyridone,
d. 3-(α-iminobenzyl)-4-hydroxy-6-(p-chlorophenyl)-1-methyl-2-(1H)-pyridone,
e. 3-(α-iminobenzyl)-4-hydroxy-6-(p-fluorophenyl)-1-methyl-2-(1H)-pyridone,
f. 3-(α-iminobenzyl)-4-hydroxy-6-(m-fluorophenyl)-1-methyl-2H-pyridone,
g. 3-(α-iminobenzyl)-4-hydroxy-6-(o-fluorophenyl)-1-methyl-2-(1H)-pyridone,
h. 3-(1-iminopropyl)-4-hydroxy-6-(p-chlorophenyl)-1-methyl-2-(1H)-pyridone,
i. 3-(1-iminopropyl)-4-hydroxy-6-(p-fluorophenyl)-1-methyl-2(1H)-pyridone,
j. 3-(1-iminopropyl)-4-hydroxy-6-(m-fluorophenyl)-1-methyl-2(1H)-pyridone,
k. 3-(1-iminopropyl)-4-hydroxy-6-(o-fluorophenyl)-1-methyl-2(1H)-pyridone, or
l.3-(α-imino-p-fluorobenzyl)-4-hydroxy-6-(p-fluorophenyl)-1-methyl-2(1H)-pyridone
there is obtained
a. 6-methyl-4-(p-chlorophenyl)-7-phenyl-2H-pyrido[3,4-e]-1,3-oxazine-2,5-dione,
b. 6-methyl-4-(p-fluorophenyl)-7-phenyl-2H-pyrido[3,4-e]-1,3-oxazine-2,5-dione,
c. 6-methyl-4-ethyl-7-phenyl-2H-pyrido[3,4-e]-1,3-oxazine-2,5-dione,
d. 6-methyl-4-phenyl-7-(p-chlorophenyl)-2H-pyrido[3,4-e]-1,3-oxazine-2,5-dione,
e. 6-methyl-4-phenyl-7-(p-fluorophenyl)-2H-pyrido[3,4-e]-1,3-oxazine-2,5-dione,
f. 6-methyl-4-phenyl-7-(m-fluorophenyl)-2H-pyrido[3,4-e]-1,3-oxazine-2,5-dione,
g. 6-methyl-4-phenyl-7-(o-fluorophenyl)-2H-pyrido[3,4-e]-1,3-oxazine-2,5-dione,
h. 6-methyl-4-ethyl-7-(p-chlorophenyl)-2H-pyrido[3,4-e]-1,3-oxazine-2,5-dione,
i. 6-methyl-4-ethyl-7-(p-fluorophenyl)-2H-pyrido[3,4-e]-1,3-oxazine-2,5-dione,
j. 6-methyl-4-ethyl-7-(m-fluorophenyl)-2H-pyrido[3,4-e]-1,3-oxazine-2,5-dione,
k. 6-methyl-4-ethyl-7-(o-fluorophenyl)-2H-pyrido[3,4-e]-1,3-oxazine-2,5-dione, or
l. 6-methyl-4-(p-fluorophenyl)-7-(p-fluorobenzyl)-2H-pyrido[3,4-e]-1,3-oxazine-2,5-dione, respectively.

The 6-methyl-4,7-diphenyl-2H-pyrido[3,4-e]-1,3-oxazine-2,5-dione of this example is an effective muscle relaxant and minor tranquilizer when orally administered to an animal in need of said treatment at a dosage of 100 mg. two to four times per day. The compound of this example is also effective as a sleep inducer when orally administered to an animal in need of said treatment at a dosage of 200 mg. just before bedtime.

What is claimed is:

1. A compound of the formula

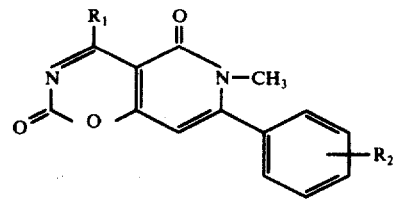

where $R_1$ represents straight chain lower alkyl or

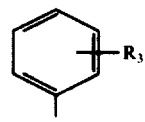

where $R_3$ represents hydrogen or halo having an atomic weight of about 19 to 36, and $R_2$ represents hydrogen or halo.

2. The compound of claim 1 of the formula

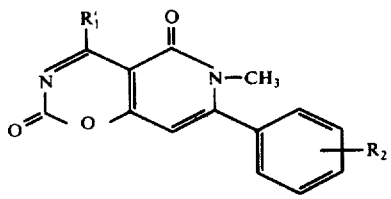

where
R$_1'$ is straight chain lower alkyl.

3. The compound of claim 1 having the formula

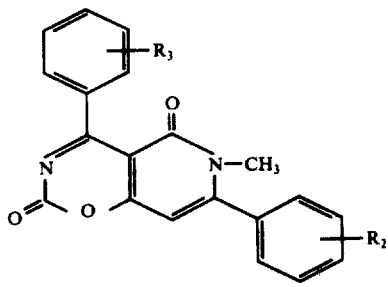

4. The compound of claim 2 which is 6-methyl-4-ethyl-7-phenyl-2H-pyrido[3,4-e]-1,3-oxazine-2,5-dione.

5. The compound of claim 3 which is 6-methyl-4,7-diphenyl-2H-pyrido[3,4-e]-1,3-oxazine-2,5-dione.

6. A method of inducing sleep which comprises administering to a mammal in need of said treatment a sleep-inducing effective amount of a compound of claim 1.

7. A method of treating tension which comprises administering to a mammal in need of said treatment a tranquilizing effective amount of a compound of claim 1.

8. A method of treating anxiety which comprises administering to mammal in need of said treatment a tranquilizing effective amount of a compound of claim 1.

9. A method of treating muscle spasms which comprises administering to a mammal in need of said treatment a muscle-relaxant effective amount of a compound of claim 1.

10. A pharmaceutical composition for use in the treatment of insomnia, muscle tension or anxiety which comprises a therapeutically effective amount of a compound of claim 1 and a pharmaceutically acceptable carrier therefor.

* * * * *